United States Patent
Menke et al.

(10) Patent No.: US 6,387,849 B1
(45) Date of Patent: May 14, 2002

(54) HERBICIDAL HYDROXIMIC ACID DERIVATIVES

(75) Inventors: Olaf Menke, Altleiningen; Gerhard Hamprecht, Weinheim; Markus Menges, Bensheim; Robert Reinhard, Ludwigshafen; Peter Schäfer, Ottersheim; Cyrill Zagar, Ludwigshafen; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/381,474
(22) PCT Filed: Mar. 12, 1998
(86) PCT No.: PCT/EP98/01440
§ 371 Date: Sep. 21, 1999
§ 102(e) Date: Sep. 21, 1999
(87) PCT Pub. No.: WO98/42681
PCT Pub. Date: Oct. 1, 1998

(30) Foreign Application Priority Data

Mar. 25, 1997 (DE) .......................... 197 12 408

(51) Int. Cl.⁷ ................. C07D 239/54; A01N 43/54
(52) U.S. Cl. ................. 504/243; 544/310; 544/311; 558/3; 558/7
(58) Field of Search ............... 544/310, 311; 504/243; 558/3, 7

(56) References Cited

U.S. PATENT DOCUMENTS

| | | |
|---|---|---|
| 5,183,492 A | 2/1993 | Suchy et al. ............. 504/243 |
| 5,266,554 A | 11/1993 | Suchy et al. ............. 504/243 |
| 5,336,663 A | 8/1994 | Wenger et al. ........... 504/243 |

FOREIGN PATENT DOCUMENTS

| | | |
|---|---|---|
| DE | 44 24 791 | 1/1996 |
| EP | 408 382 | 1/1991 |
| EP | 473 551 | 3/1992 |
| WO | 91/00278 | 1/1991 |

*Primary Examiner*—John M. Ford
(74) *Attorney, Agent, or Firm*—Keil & Weinkauf

(57) ABSTRACT

Novel hydroximic acid derivatives I

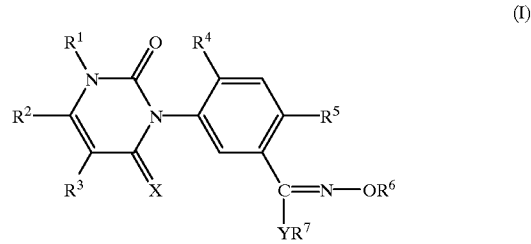

and salts thereof, where

X=O, S;
Y=O, S;
$R^1$=H, $C_1$–$C_4$-alkyl, $NH_2$, $C_1$–$C_4$-alkylamino or di($C_1$–$C_4$-alkyl)amino;
$R^2$=$C_1$–$C_3$-haloalkyl;
$R^3$=H, halogen, $C_1$–$C_4$-alkyl;
$R^4$=H, halogen;
$R^5$=CN, halogen;
$R^6$=$C_1$–$C_6$-alkyl, $C_2$–$C_6$-alkenyl, $C_3$–$C_6$-alkynyl or phenyl-$C_1$–$C_6$-alkyl, where the phenyl ring of this group may be unsubstituted or may carry 1–3 substituents;
$R^7$=a $C_1$–$C_6$-alkyl, $C_2$–$C_6$-alkenyl, $C_3$–$C_6$-alkynyl or phenyl-$C_1$–$C_6$-alkyl, where these 4 groups may be unsubstituted or may carry 1 to 2 substituents;

Use: As herbicides; for the desiccation/defoliation of plants.

18 Claims, No Drawings

HERBICIDAL HYDROXIMIC ACID DERIVATIVES

This application was filed on Sep. 21,1999, as a national phase application of International Application No. PCT/EP 98/01,440, filed Mar. 12, 1998.

The present invention relates to novel substituted hydroximic acid derivatives of the formula I

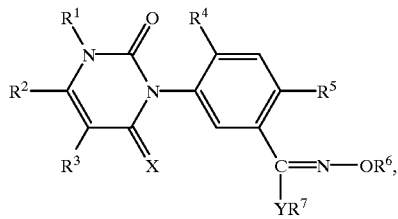

(I)

where X and the substituents $R^1$ to $R^7$ have the following meanings:

X is oxygen or sulfur;

Y is oxygen or sulfur;

$R^1$ is hydrogen, $C_1$–$C_4$-alkyl, amino, $C_1$–$C_4$-alkylamino or di($C_1$–$C_4$-alkyl)amino;

$R^2$ is $C_1$–$C_3$-haloalkyl;

$R^3$ is hydrogen, halogen or $C_1$–$C_4$-alkyl;

$R^4$ is hydrogen or halogen;

$R^5$ is cyano or halogen;

$R^6$ is $C_1$–$C_6$-alkyl, $C_2$–$C_6$-alkenyl, $C_3$–$C_6$-alkynyl or phenyl-$C_1$–$C_6$-alkyl, it being possible for the phenyl ring to be unsubstituted or to have attached to it one to three substituents each selected from the group consisting of cyano, nitro, halogen, $C_1$–$C_4$-alkyl, $C_1$–$C_6$-haloalkyl, $C_1$–$C_6$-alkoxy, $C_2$–$C_6$-alkenyloxy, $C_3$–$C_6$-alkynyloxy and ($C_1$–$C_6$-alkoxy) carbonyl;

$R^7$ is a $C_1$–$C_6$-alkyl, $C_2$–$C_6$-alkenyl, $C_3$–$C_6$-alkynyl or phenyl-$C_1$–$C_6$-alkyl group, it being possible for these 4 groups to be unsubstituted or to have attached to them one or two substituents each selected from the group consisting of halogen, $C_1$–$C_3$-alkoxy, $C_1$–$C_3$-alkoxyimino, ($C_1$–$C_3$-alkoxy)carbonyl, ($C_1$–$C_3$-alkylamino)carbonyl, di($C_1$–$C_3$-alkyl)aminocarbonyl and CO—N($C_1$–$C_3$-alkyl)-($C_1$–$C_3$-alkoxy), it being possible for the 4 last-mentioned radicals, in turn, to have attached to them a ($C_1$–$C_3$-alkoxy)carbonyl or $C_1$–$C_4$-alkoxy group;

and the agriculturally useful salts of the compounds I.

Furthermore, the invention relates to the use of the compounds I as herbicides and/or for the desiccation/defoliation of plants, herbicidal compositions and compositions for the desiccation/defoliation of plants which comprise compounds I as active substances, processes for preparing the compounds I and herbicidal compositions and compositions for the desiccation/defoliation of plants using the compounds I, methods for controlling undesirable vegetation and for the desiccation/defoliation of plants using the compounds I, and novel intermediates of the formula VII.

EP-A 408 382 disclosess herbicidally active hydroximic acid derivatives of the formula

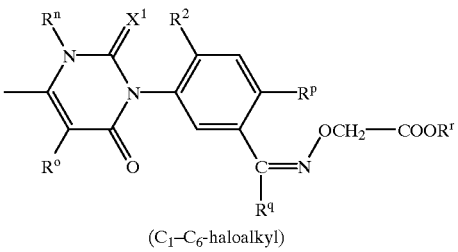

(II)

($C_1$–$C_6$-haloalkyl)

where $R^n$ is hydrogen, hydroxymethyl or $C_1$–$C_3$-[halo]alkyl, $R^o$ is hydrogen, nitro, halogen, $C_1$–$C_6$-[halo]alkyl or hydroxymethyl, $R^p$ is nitro, cyano or halogen, $R^q$ is hydrogen, $C_1$–$C_3$-alkyl, -alkoxy or -alkoxy-$C_1$–$C_2$-alkyl and $R^r$ is hydrogen, $C_1$–$C_4$-alkyl, $C_2$–$C_3$-haloalkyl, $C_3$–$C_6$-cycloalkyl, phenyl or benzyl.

DE-A 44 24 791 discloses certain hydroximic acids of cinnamic acid.

It is an object of the present invention to provide novel hydroximic acid derivatives which have a good herbicidal action. The object also extends to providing novel compounds which act as desiccants/defoliants.

We have found that this object is achieved in accordance with the invention by the hydroximic acid derivatives of the formula I. preferred compounds of the formula I can be seen from the sub-claims and from the description which follows.

Depending on the substitution pattern, the compounds of the formula I can contain one or more chiral centers, in which case they exist in the form of enantiomer or diastereomer mixtures. This invention provides both the pure enantiomers or diasteromers and mixtures thereof.

Agriculturally useful salts are in particular the salts of those cations and the acid addition salts of those acids whose cations and anions, respectively, do not adversely affect the herbicidal activity of the compounds I. Suitable cations are therefore in particular the ions of the alkali metals, preferably sodium and potassium, of the alkaline earth metals, preferably calcium, magnesium and barium, and of the transition metals, preferably manganese, copper, zinc and iron, and the ammonium ion, which may carry one to four $C_1$–$C_4$-alkyl substituents, and/or one phenyl or benzyl substituent, preferably diisopropylammonium, tetramethylammonium, tetrabutylammonium, trimethylbenzylammonium, and furthermore phosphonium ions, sulfonium ions, preferably tri($C_1$–$C_4$-alkyl)sulfonium and sulfoxonium ions, preferably tri($C_1$–$C_4$-alkyl) sulfoxonium.

Anions of useful acid addition salts are primarily chloride, bromide, fluoride, hydrogensulfate, sulfate, dihydrogenphosphate, hydrogenphosphate, phosphate, nitrate, hydrogencarbonate, carbonate, hexafluorosilicate, hexafluorophosphate, benzoate, and the anions of $C_1$–$C_4$-alkanoic acids, preferably formate, acetate, propionate and butyrate.

The organic moieties mentioned for the substituents $R^1$ to $R^3$, $R^6$, $R^7$ or as radicals on phenyl rings are collective terms for individual enumerations of each of the group members, as is the meaning halogen. All carbon chains, ie. all alkyl, haloalkyl, alkenyl, alkynyl, alkoxy, alkenyloxy, alkynyloxy, alkylamino and phenylalkyl moieties can be straight-chain or branched.

Halogenated substituents preferably have attached to them one to five identical or different halogen atoms.

Examples of individual meanings are:

halogen: fluorine, chlorine, bromine or iodine, preferably fluorine or chlorine;

$C_1$–$C_4$-alkyl; $CH_3$, $C_2H_5$, $CH_2$–$C_2H_5$, $CH(CH_3)_2$, n-$C_4H_9$, $CH(CH_3)$—$C_2H_5$, $CH_2$—$CH(CH_3)_2$ or $C(CH_3)_3$;

$C_1$–$C_6$-alkyl and the alkyl moiety of $C_1$–$C_6$-alkoxy-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl, in particular methyl or ethyl;

$C_1$–$C_6$-haloalkyl: $C_1$–$C_6$-alkyl as mentioned above which is partially or fully substituted by fluorine, chlorine, bromine and/or iodine, eg. $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 3-fluoropropyl, 3-chloropropyl or $CF_2$–$C_2F_5$, preferably $C_1$–$C_4$-haloalkyl, in particular trifluoromethyl or 1,2-dichloroethyl;

$C_2$–$C_6$-alkenyl: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-2-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut--en-1-yl, 1-ethylbut-2-en-1-yl, 1-ethylbut-3-en-1-yl, 2-ethylbut-2-en-1-yl, 2-ethylbut-2-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl, preferably $C_3$- or $C_4$-alkenyl;

$C_3$–$C_6$-alkynyl: prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably $C_3$- or $C_4$-alkynyl, in particular prop-2-yn-3-yl;

phenyl-$C_1$–$C_6$-alkyl: for example benzyl, 1-phenyleth-1-yl, 2-phenyleth-1-yl, 1-phenylprop-1-yl, 2-phenylprop-1-yl, 3-phenylprop-1-yl, 1-phenylprop-2-yl, 2-phenylprop-2-yl, 1-phenylbut-1-yl, 2-phenylbut-1-yl, 3-phenylbut-1-yl, 4-phenylbut-1-yl, 1-phenylbut-2-yl, 2-phenylbut-2-yl, 1-phenylbut-3-yl, 2-phenylbut-3-yl, 1-phenyl-2-methylprop-3-yl, 2-phenyl-2-methylprop-3-yl, 3-phenyl-2-methylprop-3-yl or 2-benzylprop-2-yl, preferably phenyl-$C_1$–$C_4$-alkyl, in particular 2-phenyleth-1-yl;

$C_1$–$C_3$-alkoxy and the alkoxy moieties of ($C_1$–$C_3$-alkoxy) carbonyl and CO—N($C_1$–$C_3$-alkyl)-($C_1$–$C_3$-alkoxy): $OCH_3$, $OC_2H_5$, $OCH_2$–$C_2H_5$ or $OCH(CH_3)_2$;

$C_1$–$C_6$-alkoxy and the alkoxy moiety of $C_1$–$C_6$-Alkoxy-$C_1$–$C_6$-alkyl: methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably $C_1$–$C_4$-alkoxy, in particular $OCH_3$, $OC_2H_5$ or $OCH(CH_3)_2$;

($C_1$–$C_6$-alkoxy)carbonyl: $COOCH_3$, $COOC_2H_5$, $COOCH_2$–$C_2H_5$, $COOCH(CH_3)_2$, $COO$(n-$C_4H_9$), $COOCH(CH_3)$—$C_2H_5$, $COOCH_2$—$CH(CH_3)_2$, $COOC(CH_3)_3$, $COO$(n-$C_{511}$), 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, preferably ($C_1$–$C_4$-alkoxy) carbonyl, in particular $COOCH_3$, $COOC_2H_5$ or $COOCH(CH_3)_2$;

$C_2$–$C_6$-alkenyloxy: ethenyloxy, prop-1-en-1-yloxy, prop-2-en-1-yloxy, 1-methylethenyloxy, n-buten-1-yloxy, n-buten-2-yloxy, n-buten-3-yloxy, 1-methylprop-1-en- 1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-Hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-3-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular prop-2-en-1-yloxy;

$C_3$–$C_6$-alkynyloxy: prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methyl-but-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular prop-2-yn-1-yloxy;

$C_1$–$C_4$-alkylamino: NH—CH$_3$, NH—C$_2$H$_5$, NH—CH$_2$—C$_2$H$_5$, NH—CH(CH$_3$)$_2$, NH-(n-C$_4$H$_9$), NH—CH(CH$_3$)—C$_2$H$_5$, NH—CH$_2$—CH(CH$_3$)$_2$ or NH—C(CH$_3$)$_3$;

($C_1$–$C_3$-alkylamino)carbonyl: CO—NH—CH$_3$, CO—NH—C$_2$H$_5$, CO—NH—CH$_2$—C$_2$H$_5$ or CO—NH—CH(CH$_3$)$_2$, in particular CO—NH—CH$_3$ or CO—NH—C$_2$H$_5$;

di($C_1$–$C_3$-alkyl)amino: N(CH$_3$)$_2$, N(C$_2$H$_5$)$_2$, N(n-C$_3$H$_7$)$_2$, N[CH(CH$_3$)$_2$]$_2$, N(n-C$_4$H$_9$)$_2$, N[CH(CH$_3$)—C$_2$H$_5$]$_2$, N[CH$_2$—CH(CH$_3$)$_2$]$_2$, N[C(CH$_3$)$_3$]$_2$, N(CH$_3$)—C$_2$H$_5$, N(CH$_3$)—CH$_2$—C$_2$H$_5$, N(CH$_3$)—CH(CH$_3$)$_2$, N(CH$_3$)-(n-C$_4$H$_9$), N(CH$_3$)—CH(CH$_3$)—C$_2$H$_5$, N(CH$_3$)—CH$_2$—CH(CH$_3$)$_2$, N(CH$_3$)—C(CH$_3$)$_3$, N(C$_2$H$_5$)—CH$_2$—C$_2$H$_5$, N(C$_2$H$_5$)—CH(CH$_3$)$_2$, N(C$_2$H$_5$)-(n-C$_4$H$_9$), N(C$_2$H$_5$)—CH(CH$_3$)—C$_2$H$_5$, N(C$_2$H$_5$)—CH$_2$—CH(CH$_3$)$_2$, N(C$_2$H$_5$)—C(CH$_3$)$_3$, N(n-C$_3$H$_7$)—CH(CH$_3$)$_2$, N(N—C$_3$H$_7$)-(n-C$_4$H$_9$), N(n-C$_3$H$_7$)—CH(CH$_3$)—C$_2$H$_5$, N(n-C$_3$H$_7$)—CH$_2$—CH(CH$_3$)$_2$, N(n-C$_3$H$_7$)—C(CH$_3$)$_3$, N[CH(CH$_3$)$_2$]-(n-C$_4$H$_9$), N[CH(CH$_3$)$_2$]—CH(CH$_3$)—C$_2$H$_5$, N[CH(CH$_3$)$_2$]—CH$_2$—CH(CH$_3$)$_2$, N[CH(CH$_3$)$_2$]—C(CH$_3$)$_3$, N(n-C$_4$H$_9$)—CH(CH$_3$)—C$_2$H$_5$, N(n-C$_4$H$_9$)—CH$_2$—CH(CH$_3$)$_2$, N(n-C$_4$H$_9$)—C(CH$_3$)$_3$, N[CH(CH$_3$)—C$_2$H$_5$]—CH$_2$—CH(CH$_3$)$_2$, N[C(CH$_3$)$_3$]—CH(CH$_3$)—C$_2$H$_5$ or N[C(CH$_3$)$_3$]—CH$_2$—CH(CH$_3$)$_2$, in particular N(CH$_3$)$_2$ or N(C$_2$H$_5$)$_2$;

di($C_1$–$C_3$-alkyl)aminocarbonyl: CO—N(CH$_3$)$_2$, CO—N(C$_2$H$_5$)$_2$, CO—N(n-C$_3$H$_7$)$_2$, CO—N[CH(CH$_3$)$_2$]$_2$, CO—N(CH$_3$)—C$_2$H$_5$, CO—N(CH$_3$)—CH$_2$—C$_2$H$_5$, CO—N(CH$_3$)—CH(CH$_3$)$_2$, CO—N(C$_2$H$_5$)—CH$_2$—C$_2$H$_5$, CO—N(C$_2$H$_5$)—CH(CH$_3$)$_2$ or CO—N(n-C$_3$H$_7$)—CH(CH$_3$)$_2$, in particular CO—N(CH$_3$)$_2$ or CO—N(C$_2$H$_5$)$_2$;

$C_1$–$C_3$-alkoxyimino: methoxyimino, ethoxyimino, n-propyloxyimino or i-propyloxyimino.

preferred compounds I are those where the substituents have the following meanings:

X is oxygen;

$R^1$ is methyl or amino;

$R^2$ is trifluoromethyl or trifluoroethyl;

$R^3$ is hydrogen;

$R^4$ is halogen, in particular fluorine;

$R^5$ is cyano or chlorine;

$R^6$ is $C_1$–$C_6$-alkyl, $C_3$–$C_6$-alkenyl, $C_3$–$C_6$-alkynyl or phenyl-$C_1$–$C_6$-alkyl, it being possible for the phenyl ring to have attached to it one to three substituents each selected from the group consisting of cyano, nitro, halogen, $C_1$–$C_4$-alkyl, $C_1$–$C_4$-haloalkyl, $C_1$–$C_4$-alkoxy, $C_3$–$C_5$-alkenyloxy and $C_3$–$C_5$-alkynyloxy; $R^6$ is, in particular, $C_1$–$C_4$-alkyl or phenyl-$C_1$–$C_4$-alkyl, it being possible for the phenyl ring to have attached to it one to three substituents each selected from the group consisting of cyano, nitro, halogen, $C_1$–$C_4$-alkyl, $C_1$–$C_4$-haloalkyl, $C_1$–$C_4$-alkoxy, $C_3$–$C_5$-alkenyloxy and $C_3$–$C_5$-alkynyloxy;

$R^7$ is $C_1$–$C_4$-alkyl having one or two substituents each selected from the group consisting of $C_1$–$C_3$-alkoxyimino, ($C_1$–$C_3$-alkoxy)carbonyl, ($C_1$–$C_3$-alkylamino)carbonyl, di($C_1$–$C_3$-alkyl)aminocarbonyl and CO—N($C_1$–$C_3$-alkyl)-($C_1$–$C_3$-alkoxy), it being additionally possible for the last four radicals, in turn, to have attached to them a ($C_1$–$C_3$-alkoxy)carbonyl group.

Compounds of the formula I, where $R^1$ to $R^5$ have the meanings mentioned in Table 1 and $R^6$ and $R^7$ represent in each case one row of Tables 2 and 3, respectively, are particularly preferred.

TABLE 1

| No. | $R^1$ | $R^2$ | $R^3$ | $R^4$ | $R^5$ |
|---|---|---|---|---|---|
| 1.1 | CH$_3$ | CF$_3$ | H | F | Cl |
| 1.2 | CH$_3$ | CF$_3$ | H | F | CN |
| 1.3 | CH$_3$ | CF$_3$ | H | H | Cl |
| 1.4 | CH$_3$ | CF$_3$ | H | H | CN |
| 1.5 | NH$_2$ | CF$_3$ | H | F | Cl |

TABLE 1-continued

| No. | $R^1$ | $R^2$ | $R^3$ | $R^4$ | $R^5$ |
|---|---|---|---|---|---|
| 1.6 | $NH_2$ | $CF_3$ | H | F | CN |
| 1.7 | $NH_2$ | $CF_3$ | H | H | Cl |
| 1.8 | $NH_2$ | $CF_3$ | H | H | CN |

TABLE 2

| No. | $R^6$ |
|---|---|
| 2.1 | $CH_3$ |
| 2.2 | $C_2H_5$ |
| 2.3 | $CH(CH_3)CH_3$ |
| 2.4 | $CH_2CH=CH_2$ |
| 2.5 | $CH_2C\equiv CH$ |
| 2.6 | $CH(CH_3)C\equiv CH$ |
| 2.7 | $CH_2C_6H_5$ |

TABLE 3

| No. | $R^7$ |
|---|---|
| 3.1 | $CH_3$ |
| 3.2 | $CH_2CH=CH_2$ |
| 3.3 | $CH_2C\equiv CH$ |
| 3.4 | $CH_2COOCH_3$ |
| 3.5 | $CH_2COOC_2H_5$ |
| 3.6 | $CH_2COOCH_2CH_2CH_3$ |
| 3.7 | $CH_2COOCH_2COOCH_3$ |
| 3.8 | $CH_2CON(OCH_3)CH_3$ |
| 3.9 | $CH_2-C_6H_5$ |
| 3.10 | $CH_2C(NOCH_3)COOCH_3$ |
| 3.11 | $CH(CH_3)CH_3$ |
| 3.12 | $CH(CH_3)C\equiv CH$ |
| 3.13 | $CH(CH_3)COOCH_3$ |
| 3.14 | $CH(CH_3)COOCH_2CH_3$ |
| 3.15 | $CH(CH_3)CON(OCH_3)CH_3$ |

Compound 1.1. of Table 1 where $R^6$ has the meaning of 2.1. and $R^7$ has the meaning of 3.3. is cited hereinbelow as 1.1./2.1./3.3. The hydroximic acid derivatives I according to the invention are obtainable by various routes, preferably by one of the processes described hereinbelow.

a) Alkylation of a Hydroxamic Acid Derivative of the Formula III:

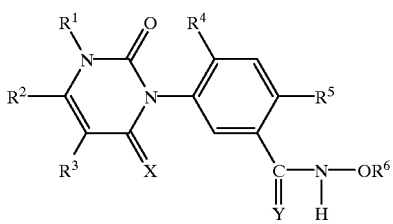

(III)

As a rule, the process is carried out in an inert solvent or diluent, preferably in the presence of a base.

Examples of suitable solvents are protic solvents, such as the lower alcohols, preferably ethanol, if desired, as a mixture with water, or aprotic solvents such as aliphatic or cyclic ethers, preferably 1,2-dimethoxyethane, tetrahydrofuran and dioxane, aliphatic ketones, preferably acetone, amides, preferably dimethylformamide, sulfoxides, preferably dimethylsulfoxide, ureas such as tetramethylurea and 1,3-dimethyltetrahydro-2(1H)pyrimidinone, carboxylic esters such as ethyl acetate, or halogenated aliphatic or aromatic hydrocarbons such as dichloromethane and chlorobenzene.

Alkylation is normally carried out with the halide, preferably chloride or bromide, the sulfate, a sulfonate, preferably a methanesulfonate (mesylate) such as trifluoromethanesulfonate (triflate) or a benzenesulfonate such as p-toluenesulfonate (tosylate) and p-bromobenzenesulfonate (brosylate), or with a diazo compound, eg. diazomethane.

Suitable bases are inorganic bases, eg. carbonates, such as potassium carbonate and sodium carbonate, hydrogen carbonates such as potassium hydrogen carbonate and sodium hydrogen carbonate, alkali metal hydrides such as sodium hydride and potassium hydride, and organic bases, eg. amines, such as triethylamine, pyridine and N,N-diethylaniline, or alkali metal alkoxides such as sodium methoxide, sodium ethoxide and potassium tert-butoxide.

It is preferred to use 0.5 to 2 times the molar amount of both base and alkylating agent, based on the amount of III.

In general, a reaction temperature of from (–78° C.) to the boiling point of the reaction mixture, in particular from (–60) to 60° C., is suitable.

Alkylation of the compounds of the formula III normally gives not only substituted hydroximic acid derivatives I according to the invention, but also the corresponding amide-nitrogen-substituted cinnamohydroxamide derivatives. The ratio in which the two products are formed depends on the reaction temperature, on the alkylating agent, the base used and also on the particular starting compound III. The desired compound I can normally be separated from the by-products in a manner known per se, eg. by crystallization or chromatography.

b) Alkylation of a Substituted Hydroximic Acid IV Which Corresponds to the Formula I with Hydrogen on Place of $R^6$:

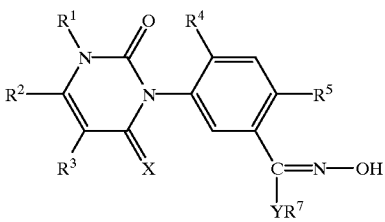

(IV)

As regards the reaction conditions, what has been said above for process variant a) also applies here.

c) Reaction of a Hydroximino Halide of the Formula V with an Alcohol or Thiol Derivative

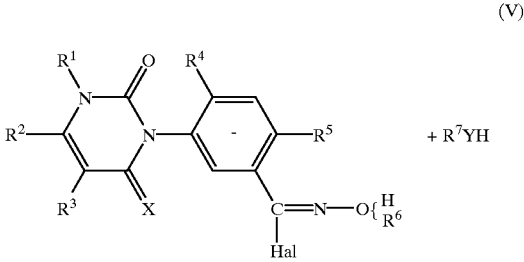

(V)

It is advantageous to use, as alcohol/thiol derivatives, the alcohols/thiols $R^7YH$ or their salts, in particular those of the alkali metals or alkaline earth metals.

Examples of suitable solvents or diluents are aliphatic or cyclic ethers such as diethyl ether and tetrahydrofuran, aliphatic ketones such as acetone, hydrocarbons such as n-pentane, cyclohexane and petroleum ether, aromatic hydrocarbons such as benzene and toluene, halogenated aliphatic or aromatic hydrocarbons such as dichloromethane and chlorobenzene, esters such as ethyl acetate, amides such as dimethylformamide and N-methylpyrrolidone, sulfoxides such as dimethyl sulfoxide, and mixtures of these. The alcohols and alcohol derivatives themselves are also suitable as solvents or diluents.

The ratio of V to alcohol/thiol or alcohol/thiol derivative $R^7YH$ is not critical. Approximately equimolar amounts are normally employed. However, it may also be expedient to employ an excess of the alcohol/thiol or the alcohol/thiol derivative, so that it acts simultaneously as solvent or diluent.

In general, a reaction temperature of from (−78)° C. to the boiling point of the particular reaction mixture is suitable, in particular from 0 to 80° C.

The reaction of V with an alcohol/thiol $R^7YH$ or a derivative thereof is particularly advantageously carried out in the presence of a base, suitable bases being not only inorganic bases, eg. carbonates, hydrogen carbonates or alkali metal hydrides, but also organic bases, eg. amines such as triethylamine, pyridine and N,N-dimethylaniline, or alkali metal alkoxides. An alkoxide/thiolate of the alcohol/thiol $R^7YH$ is expediently used as the base.

The base can be employed in catalytic, substoichiometric or stoichiometric amounts or in excess of up to five times the molar amount, based on V.

The hydroximino halides of the formula V are obtainable for example by halogenating the corresponding carbonyl compounds of the formula III.

This halogenation reaction is normally carried out in an inert solvent or diluent, suitable substances being, in particular, aprotic, organic liquids, for example aliphatic or aromatic hydrocarbons, such as n-hexane benzene, toluene and o-, m- and p-xylene, halogenated aliphatic hydrocarbons such as methylene chloride, chloroform and 1,2-dichloroethane, halogenated aromatic hydrocarbons, such as chlorobenzene, tertiary amines such as N,N-dimethylaniline, or nitriles such as acetonitrile.

Suitable halogenating agents are, above all, thionyl chloride, phosphorus pentachloride, phosphorus oxychloride, phosphorus pentabromide or phosphorus oxybromide. The use of a mixture of phosphorus pentachloride and phosphorus oxychloride or of phosphorus pentabromide and phosphorus oxybromide may also be particularly advantageous, in which case the process can be carried out without diluent in an excess of phosphorus oxychloride or phosphorus oxybromide.

When using thionyl chloride as the halogenating agent, it is recommended to add a catalytic amount of dimethylformamide.

A mixture of a tetrahalomethane, such as carbon tetrachloride and carbon tetrabromide, and an unsubstituted or substituted triphenylphosphane, eg. triphenylphosphane or tri-(o-tolyl)phosphane has proved particularly suitable.

At least equimolar amounts of halogenating agent and starting compound III are required for complete reaction. In general, an excess of halogenating agent of up to approximately eight times the molar amount, based on III, has a favorable effect on the course of the reaction.

In general, the reaction temperature is from 0° C. to the reflux temperature of the reaction mixture, preferably at from 20 to 120° C.

d) Conversion of a Nitrile of the Formula VI into a Compound of the Formula I in two Steps:

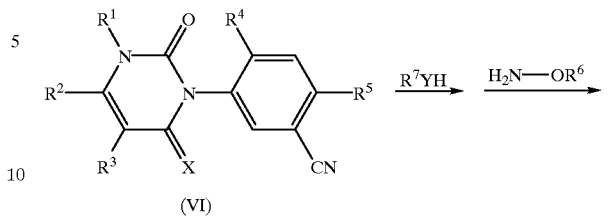

(VI)

I

The reaction is normally carried out in two steps by first reacting the nitrile VI with an alcohol/thiol $R^7YH$ and then reacting the resulting imido ester with an hydroxylamine $H_2N$—$OR^6$, if desired without isolating the imido ester from the reaction mixture.

VI can be reacted with $R^7YH$ in an inert solvent or diluent or in the absence of a solvent in an excess of the alcohol/thiol. An acidic or "Lewis"-acidic catalyst is frequently beneficial, preferably in an approximately catalytic amount or in an amount of up to approximately 200 mol %, based on the amount of VI.

Particularly suitable inert solvents or diluents are organic solvents, eg. aliphatic or cyclic ethers such as diethyl ether, tetrahydrofuran and dimethoxyethane, aliphatic, cyclic or aromatic hydrocarbons such as n-pentane, petroleum ether, cyclohexane, toluene and the xylenes, amides such as. dimethylformamide and N-methylpyrrolidone, halogenated hydrocarbons such as dichloromethane, chlorobenzene and 1,2-dichloromethane, or mixtures of these.

Suitable acidic catalysts are inorganic, preferably anhydrous, acids, eg. hydrogen chloride, hydrogen bromide, nitric acid, sulfuric acid, also oleum, or perchloric acid, and organic acids such as acetic acid, propionic acid, p-toluenesulfonic acid and trifluoroacetic acid. Examples of "Lewis"-acidic catalysts are titanium tetrachloride, tin(II) chloride, iron(III) chloride, aluminum trichloride, ethylaluminum dichloride, titanium tetraisopropoxide and boron trifluoroetherate.

The amount of $R^7YH$ is not critical. Normally, 1 to 10 mol of alcohol/thio per mole of VI suffice for an optimum reaction of VI. If the process is carried out in the alcohol/thiol in question in the absence of a solvent, this alcohol may also be present in a larger excess.

If the imido ester is obtained in salt form in the first step, it is recommended to liberate the neutral compound before carrying out the reaction of hydroxylamine $H_2N$—$OR^6$.

Hydroxylamines which are obtainable in the form of their salts, in particular as hydrochlorides, hydrobromides or sulfates, or which are obtained in salt form during the preparation can be liberated by adding a suitable base before they are reacted, especially suitable bases being those mentioned for method a).

The resulting imido ester with $H_2N$—$OR^6$ is generally reacted in an inert solvent or diluent. Suitable substances are also alcohols such as methanol, ethanol and isopropanol, nitriles such as acetonitrile, amines such as triethylamine, pyridine and N,N-dimethylaniline, or else water besides the abovementioned solvents.

It is expedient to react imido ester and hydroxylamine with each other in approximately equimolar amounts. To react the imido ester as completely as possible, however, it may be advantageous to employ the hydroxylamine $H_2N$—$OR^6$ in an excess, of up to approximately 10 mol %.

For both steps, the reaction temperature is generally at from (−20) to 120° C., in particular at from 0° C. to the boiling point of the reaction mixture.

e) Conversion of an Oxime of the Formula VII

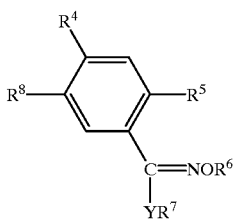

(VII)

where $R^8$ is nitro, amino, isocyanato, isothiocyanato, $(C_1-C_6\text{-alkyl})$carbamato or phenylcarbamato
  into the hydroximic acid derivatives of the formula I according to the invention by a method described in wo 93/06090.

The compounds of the formula VII are novel. They themselves are obtainable by one of the processes described above for the preparation of compounds I.

f) Sulfurization of a Hydroximic Acid Derivative of the Formula I Where X=Oxygen:

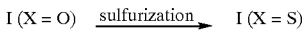

I (X = O) —sulfurization→ I (X = S)

The sulfurization is generally carried out in an inert solvent or diluent, for example in an aromatic hydrocarbon such as toluene or a xylene, in an ether such as diethyl ether, 1,2-dimethoxyethane and tetrahydrofuran, or in an organic amine such as pyridine.

Particularly suitable sulfurizing agents are phosphorus (V) sulfide and 2,4-bis(4-methoxyphenyl)-1,3,2,4-dithiadiphosphetane-2,4-dithione ("Lawesson's Reagent").

Usually 1 to 5 times the molar amount, based on the starting material to be sulfurized, is sufficient for virtually complete conversion.

The reaction temperature is generally from 20 to 200° C., preferably from 40° C. to the boiling point of the reaction mixture.

The hydroxamic acid derivatives of the formula III where Y=oxygen are accessible for example from benzoic acids of the formula VIII:

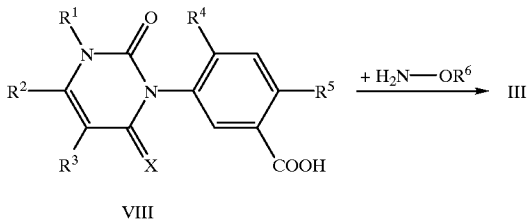

VIII

The reaction is normally carried out in an inert solvent or diluent in the presence of a condensation auxiliary or without solvent in an excess of the condensation auxiliary.

Especially suitable solvents or diluents are organic solvents, eg. aliphatic or cyclic ethers such as diethyl ether, tetrahydrofuran and dimethoxyethane, aliphatic, cyclic or aromatic hydrocarbons such as n-pentane, petroleum ether, cyclohexane, toluene and the xylenes, alcohols such as methanol, ethanol and i-propanol, amides such as dimethylformamide and N-methylpyrrolidone, nitriles such as acetonitrile, amines such as triethylamine, pyridine and N,N-dimethylaniline, halogenated hydrocarbons such as dichloromethane, chlorobenzene and 1,2-dichloromethane, or water. Mixtures of these are also suitable.

Suitable condensation auxiliaries are, for example, oxalyl chloride, carbonyl diimidazole, carbodiimides such as dicyclohexylcarbodiimide, halogenating agents such as thionyl chloride, phoshorus oxychloride, phosgene, phosphorus trichloride and phoshorus pentachloride, or methyl or ethyl chloroformate.

Preferred is the use of an halogenating agent, first giving an acid halide "in situ", which then further reacts with the hydroxylamine $H_2N\text{—}OR^6$ to give the product III.

However, it is also possible to prepare specifically the acid halide in a separate process step and, if desired, subsequently to react it in purified form with the hydroxylamine $H_2N\text{—}OR^6$.

Hydroxylamines which are obtainable in the form of their salts, in particular as hydrochlorides, hydrobromides or sulfates, or which are obtained during preparation in salt form, can be liberated - prior to their reaction with VIII, if desired also in the reaction mixture with the condensation auxiliary and VIII-by adding a suitable base.

Bases which are especially suitable for this purpose are those mentioned for method a).

The amounts of condensation auxiliary, VIII und hydroxylamine $H_2N\text{-}OR^6$ are not critical. They are expediently used in approximately equimolar amounts of the starting materials. If desired, the condensation auxiliary may also be employed in an excess, in which case the process may even be carried out without inert solvent.

Hydroxamic acid derivatives III where Y=sulfur are advantageously obtainable by sulfurization of the corresponding derivatives III where Y=oxygen, similar to process f).

Here, the amount of sulfurizing agent can be 0.5 to 5 mol, based on 1 mole of the compound III (y=0) to be sulfurized.

All the above-described processes are expediently carried out under atmospheric pressure or under the inherent pressure of the reaction mixture in question.

As a rule, the reaction mixtures are worked up by methods known per se, for example by removing the solvent, partitioning the residue in a mixture of water and a suitable organic solvent and working up the organic phase to obtain the product.

The substituted hydroximic acid derivatives of the formula I according to the invention can be obtained from the preparation as isomer mixtures which, if desired, can be separated into the pure isomers by the methods conventionally used for this purpose, eg. by means of crystallization or chromatography on an optically active adsorbate. Pure optically active isomers can, for example, also be prepared from suitable optically active starting materials.

Substituted hydroximic acid derivatives I with C—H acidic substituents can be converted into their alkali metal salts in a manner known per se by reaction with a base of the corresponding cation.

Salts of I whose metal ion is not an alkali metal ion can normally be prepared by double decomposition of the corresponding alkali metal salt in aqueous solution.

Other metal salts, such as manganese, copper, zinc, iron, calcium, magnesium and barium salts, can be prepared from the sodium salts in the customary manner, and also ammonium and phosphonium salts by means of ammonia, phosphonium, sulfonium or sulfoxonium hydroxides.

The compounds I and their agriculturally useful salts are suitable as herbicides, both in the form of isomer mixtures and in the form of the pure isomers. The herbicidal compositions comprising I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the compounds I, or compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (S. vulgare), *Theobroma cacao, Trifolium pratense, Triticum aestivum, Triticum durum, Vicia faba, Vitis vinifera* and *Zea mays*.

Moreover, the compounds I may also be used in crops which have been made fully or partially tolerant to the action of herbicides due to breeding including genetic engineering methods.

Furthermore, the substituted hydroximic acid derivatives I are also suitable for the desiccation and/or defoliation of plants.

As desiccants, they are especially suitable for desiccating the aerial parts of crop plants such as potatoes, oilseed rape, sunflowers and soybeans. This allows completely mechanical harvesting of these important crop plants.

Also of economic interest is facilitated harvesting, which is made possible by concentrating, over a period of time, dehiscence, or reduced adhesion to the tree, in the case of citrus fruit, olives or other species and varieties of pomaceous fruit, stone fruit and nuts. The same mechanism, ie. promotion of the formation of abscission tissue between fruit or leaf and shoot of the plants, is also essential for readily controllable defoliation of useful plants, in particular cotton.

Moreover, a shortened period of time within which the individual cotton plants ripen results in an increased fiber quality after harvesting.

The compounds I, or the compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert additives are essentially: mineral oil fractions of medium to high boiling point such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, eg. amines such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substituted hydroximic acid derivatives as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the active ingredients I in the ready-to-use products can be varied within wide ranges. In general, the formulations comprise approximately from 0.001 to 98% by weight, preferably 0.01 to 95% by weight, of at least one active ingredient. The active ingredients are normally employed in a purity of from 90% to 100%, preferably 95% to 100% (according to NMR spectrum).

The formulation examples below illustrate the preparation of such formulations:

I. 20 parts by weight of the compound No. 4.01 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 4.02. are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 4.03. are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 4.04. are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 4.08. are mixed with 97 parts by weight of finely divided kaolin. This gives a dust which comprises 3% by weight of the active ingredient.

VI. 20 parts by weight of the active ingredient No. 4.09. are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 4.10 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 4.11 is dissolved in a mixture composed of 80 parts by weight of cyclohexanone and 20 parts by weight of Wettol® EM 31 (non-ionic emulsifier based on ethoxylated castor oil; BASF AG). This gives a stable emulsion concentrate.

The active ingredients I, or the herbicidal compositions comprising them, can be applied pre- or post-emergence. If the active ingredients are less well tolerated by certain crop plants, application techniques may be used in which the herbicidal compositions are sprayed, with the aid of the spray apparatus, in such a way that they come into as little contact as possible, if any, with the leaves of the sensitive crop plants while reaching the leaves of undesirable plants which grow underneath, or the bare soil (post-directed, lay-by).

Depending on the intended aim of the control measures, the season, the target plants and the growth stage, the application rates of active ingredient are from 0.001 to 3.0, preferably 0.01 to 1 kg/ha active substance (a.s.).

To widen the spectrum of action and to achieve synergistic effects, the substituted hydroximic acid derivatives I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenylderivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, in the form of a mixture with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

PREPARATION EXAMPLES

Example 1

3-[2-Fluoro-4-chloro-5-(0-allylhydroxylaminocarbonyl)-phenyl]-2,4-dioxo-1-methyl-6-trifluoromethyl-1,2,3,4-tetrahydro-pyrimidine

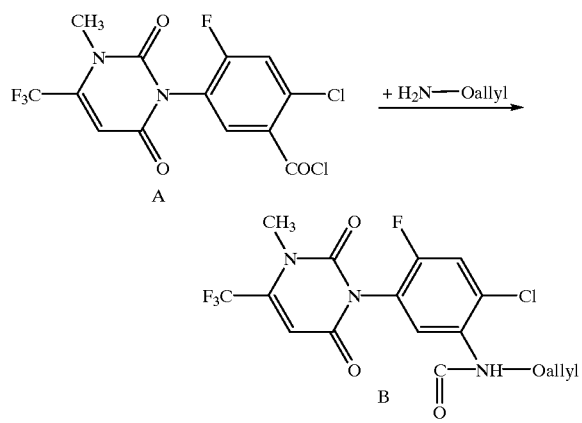

3 g of allylhydroxylamine hydrochloride monohydrate were introduced in 100 ml of toluene, and 5.6 g of triethylamine were added at room temperature (RT). To this there were added dropwise 9.6 g of A, dissolved in 80 ml of toluene, during which process the temperature of the solution climbed to 350C. The reaction solution was subsequently stirred for 5 hours at room temperature, 50 ml of water were then injected, the precipitate which had separated out was removed and washed first with 50 ml of water and then with 50 ml of petroleum ether. After the precipitation had been dried at 50° C. under reduced pressure, 5.5 g of the desired product B of melting point 152–153° C. were obtained.

Example 2

3-[2-Fluoro-4-chloro-5-(0-benzylhydroxylaminocarbonyl)-phenyl]-2,4-dioxo-1-methyl-6-trifluoromethyl-1,2,3,4-tetrahydro-pyrimidine

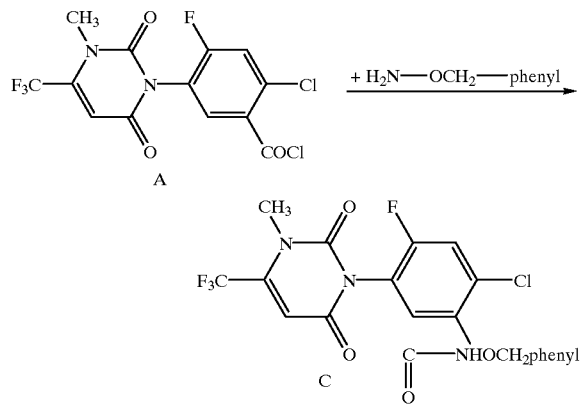

3.5 g of benzylhydroxylamine hydrochloride were introduced into 90 ml of toluene, and 4.5 g of triethylamine were added at room temperature (RT). To this there were added dropwise 7.7 g of A, dissolved in 60 ml of toluene, during which process the temperature of the solution climbed to 30° C. The reaction solution was subsequently stirred for 5 hours at room temperature and then washed 3 times with in each case 50 ml of water and dried over sodium sulfate, and the solvent was distilled off under reduced pressure. The resulting oil was purified by chromatography on silica gel using methylene chloride as the eluent, subsequently stirred with diisopropyl ether, and the precipitate which formed was filtered off and washed with petroleum ether. After the precipitate had been dried at 50° C. under reduced pressure, 5.5 g of the desired product C of melting point 114–116° C. were obtained.

Other hydroxamic acid derivatives can be prepared in a similar manner.

Example 3

Preparation of 3-[2-fluoro-4-chloro-5-methoxyimino-(allyloxy)methylphenyl]-2,4-dioxo-1-methyl-6-trifluoromethyl-1,2,3,4-tetrahydropyrimidine (Compound 4.02)

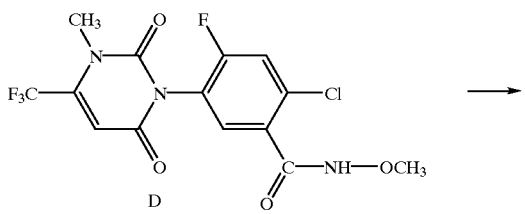

-continued

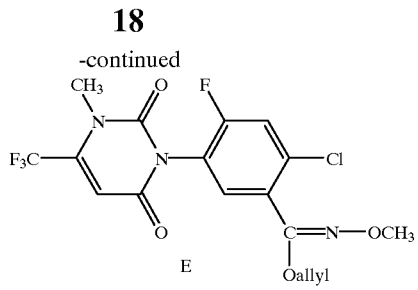

2 g of D were introduced into 80 ml of acetone, and 0.8 g of potassium carbonate were added. To this mixture there was added dropwise 0.52 g of allyl bromide, and the reaction mixture was stirred for 17 hours at room temperature (RT). The solvent was subsequently distilled off under reduced pressure, and the residue was taken up in 100 ml of methylene chloride, washed in each case three times with 30 ml of water and dried over sodium sulfate. The solid obtained after the solvent had been removed by distillation was purified by chromatography on silica gel (eluent: methylene chloride/ethyl acetate=95:5). The resulting oil was stirred with a 1:1 mixture of petroleum ether and diisopropyl ether, and the precipitate which formed was filtered off and washed with petroleum ether. After the precipitate had been dried, 0.45 g of the desired product E of melting point 73–75° C. was obtained.

Example 4

Preparation of 3-[2-fluoro-4-chloro-5-methoxyimino-(methoxy)methylphenyl]-2,4-dioxo-1-methyl-6-trifluoromethyl-1,2,3,4-tetrahydropyrimidine (Compound 4.01)

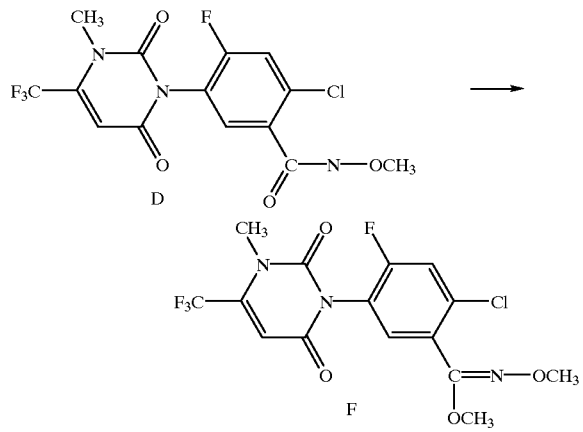

2 g of D were introduced into 100 ml of acetone, and 0.7 g of potassium carbonate was added. To this mixture there was added dropwise 0.83 ml of methyl tosylate and the reaction mixture was refluxed for 5 hours. The solvent was subsequently distilled off under reduced pressure, and the residue was taken up in 100 ml of methylene chloride, washed in each case three times with 30 ml of water and dried over sodium sulfate. The solid obtained after the solvent had been removed by distillation was purified by chromatography on silica gel (eluent: methylene chloride/ethyl acetate=90:10). The resulting oil was stirred with a 1:1 mixture of petroleum ether and diisopropyl ether, and the resulting precipitate was filtered off and washed with petroleum ether. After the precipitate had been dried, 0.65 g of the desired product F of melting point 122–1240C was obtained.

The compounds listed in Table 4 below were prepared following the above-described processes. These compounds are exemplary of the compounds of the formula I according to the invention, which can be prepared by the processes described in the Examples or in the above description.

using 3×30 ml of ethyl acetate. The combined organic phases were subsequently washed twice with water, dried over sodium sulfate and finally concentrated. The crude product was purified by medium pressure liquid chromatography (MPLC; FL eluent mixture: cyclohexane/ethyl acetate=3:1). Yield: 0.11 g of the desired compound H as a yellow, very viscous oil.

TABLE 4

I {X, Y = O; $R^1$ = $CH_3$; $R^2$ = $CF_3$; $R^3$ = H; $R^4$ = F; $R^5$ = Cl}

| No. | $R^4$ | $R^6$ | $R^7$ | m.p. (° C.) |
|---|---|---|---|---|
| 4.01 | F | $CH_3$ | $CH_3$ | 122–124 |
| 4.02 | F | $CH_3$ | $CH_2CH=CH_2$ | 73–75 |
| 4.03 | F | $CH_3$ | $CH_2C_6H_5$ | oil |
| 4.04 | F | $CH_3$ | $CH_2COOCH_3$ | oil |
| 4.05 | F | $CH_3$ | $CH(CH_3)COOCH_3$ | oil |
| 4.06 | F | $CH_2CH=CH_2$ | $CH_3$ | oil |
| 4.07 | F | $CH_2CH=CH_2$ | $CH_2CH=CH_2$ | oil |
| 4.08 | F | $CH_2CH=CH_2$ | $CH_2COOCH_3$ | 116–117 |
| 4.09 | F | $CH_2C_6H_5$ | $CH_3$ | 127–129 |
| 4.10 | F | $CH_2C_6H_5$ | $CH_2COOCH_3$ | 146–148 (cis) |
| 4.11 | F | $CH_3$ | $CH_2C(NOCH_3)COOCH_3$ | oil |
| 4.12 | F | $CH_2(o\text{-}Cl\text{—}C_6H_4)$ | $CH_2COOCH_3$ | oil |
| 4.13 | F | $CH_2\text{—}(m\text{-}Cl\text{—}C_6H_4)$ | $CH_2COOCH_3$ | oil |
| 4.14 | F | $CH_2\text{—}(p\text{-}Cl\text{—}C_6H_4)$ | $CH_2COOCH_5$ | oil |
| 4.15 | F | $CH_2\text{—}(o,m\text{-}Cl_2\text{—}C_6H_3)$ | $CH_2COOCH_3$ | oil |
| 4.16 | F | $CH_2\text{—}(m,p\text{-}Cl_2\text{—}C_6H_3)$ | $CH_2COOCH_3$ | oil |
| 4.17 | F | $CH_2\text{—}(m\text{-}CF_3\text{—}C_6H_4)$ | $CH_2COOCH_3$ | oil |
| 4.18 | F | $CH_2\text{—}C_6H_5$ | $CH_2COOCH_3$ | oil (trans) |
| 4.19 | F | $CH_2\text{—}C_6H_5$ | $CH(CH_3)COOCH_3$ | oil |

Example 5

Preparation of 3-[2-fluoro-4-chloro-5-[ethoxyimino (methylthio)-methyl]phenyl]-2,4-dioxo-1-methyl-6-trifluoromethyl-1,2,3,4-tetrahydropyrimidine Precursor
3-[2-Fluoro-4-chloro-5-(ethylhydroxylaminothiocarbonyl) phenyl-2,4-dioxo-1-methyl-6-trifluoromethyl-1,2,3,4-tetrahydropyrimidine

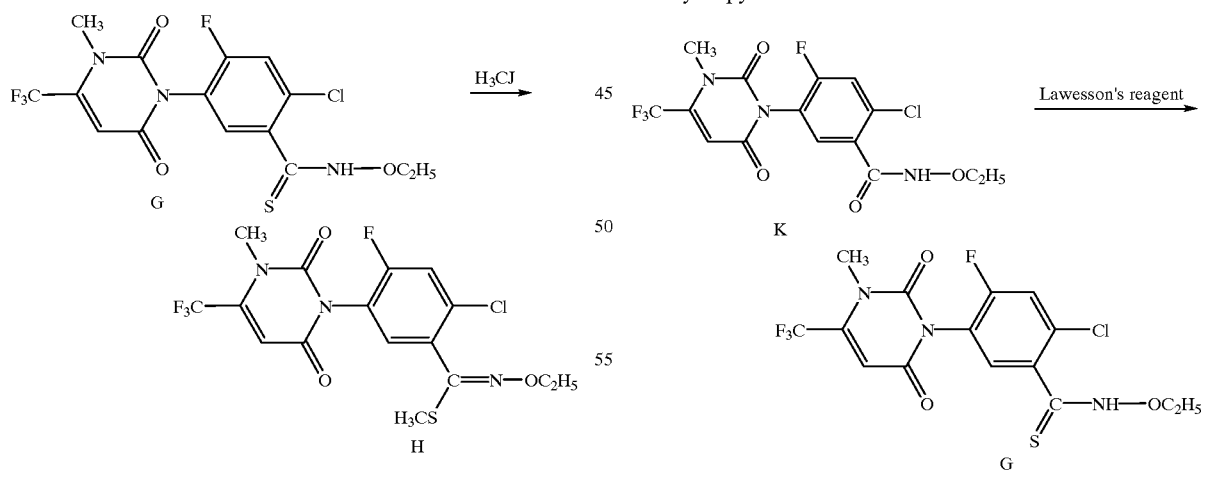

Initially 0.22 g of potassium carbonate and then 0.23 g of methyl iodide were added dropwise to 0.69 g of G in 10 ml of absolute ethanol. The mixture was stirred at room temperature (RT) for 3 hours and then the low-boiling proportions removed. The residue was admixed with 50 ml of saturated aqueous sodium bicarbonate solution. The resulting product of value was extracted from the aqueous phase A solution of 0.54 g of G and 0.27 g of Lawesson's reagent in 5 ml of absolute tetrahydrofuran was heated to reflux temperature for 12 hours. After cooling of the reaction mixture, the solvent was distilled off. The residue was admixed with 50 ml of saturated aqueous sodium bicarbonate solution. The mixture was then extracted with 3×30 ml of ethyl acetate. The combined organic phases were washed twice with water. Yield: 0.69 g of crude product which was methylated without any further purification.

In a similar manner:

3-[2-fluoro-4-chloro-5-[(2-methylpropyl)hydroxylaminothio-carbonyl]phenyl]-2,4-dioxo-1-methyl-6-trifluoromethyl-1,2,3,4-tetrahydropyrimidine gave the corresponding compound I where $YR^7=SCH_3$;

3-[2-fluoro-4-chloro-5-(propyn-3-ylhydroxylaminothiocarbonyl)phenyl]-2,4-dioxo-1-methyl-6-trifluoromethyl-1,2,3,4-tetrahydropyrimidine gave the corresponding compound I where $YR^7=SCH_3$; yield: 23%; m.p.: 68–70° C.;

3-[2-fluoro-4-chloro-5-(prop-2-ylhydroxylaminothiocarbonyl)-phenyl]-2,4-dioxo-1-methyl-6-trifluoromethyl-1,2,3,4-tetrahydropyrimidine gave the corresponding compound I where $yR^7=SCH_3$; yield: 20%; colorless oil.

Use Examples for the Herbicidal Activity

The herbicidal action of the substituted hydroximic acid derivatives I was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 7.8 or 3.9 g/ha a.s.

Depending on the species, the plants were kept at from 10–25° C. and 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific Name | Common Name |
| --- | --- |
| Amaranthus retroflexus (AMARE) | Redroot pigweed |
| Ipomoea spec. (IPOSS) | morning glory |
| Setaria faberii (SETFA) | giant foxtail |
| Setaria viridis (SETVI) | green foxtail |
| Solanum nigrum (SOLNI) | black nightshade |

At a rate of application of 7.8 or 3.9 g/ha of a.s., compound No. 4.08 showed a very good herbicidal action against undesired broad-leaved plants and grass weeds when applied post-emergence.

Use Examples for the Desiccant/defoliant Activity

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to run-off point with aqueous preparations of the active ingredients (with an addition of 0.15% by weight of the fatty alcohol alkoxylate Plurafac® LF 700[1]), based on the spray mixture). The amount of water applied was 1000 L/ha (converted). After 13 days, the number of leaves shed and the degree of defoliation in % were determined.

No leaves were shed in the untreated control plants.

1) a low-foam, nonionic surfactant from BASF AG.

We claim:

1. A hydroximic acid compound of formula I $$\text{(I)}$$

[Chemical structure of formula I showing a pyrimidine ring with substituents $R^1$, $R^2$, $R^3$, $R^4$, $R^5$, and a $C(YR^7)=N-OR^6$ group, with X in the pyrimidine ring]

wherein

X is oxygen or sulfur;

Y is oxygen or sulfur;

$R^1$ is hydrogen, $C_1–C_4$-alkyl, amino, $C_1–C_4$-alkylamino or di($C_1–C_4$-alkyl)amino;

$R^2$ is $C_1–C_3$-haloalkyl;

$R^3$ is hydrogen, halogen or $C_1–C_4$-alkyl;

$R^4$ is hydrogen or halogen;

$R^5$ is cyano or halogen;

$R^6$ is $C_1–C_6$-alkyl, $C_2–C_6$-alkenyl, $C_3–C_6$-alkynyl or is phenyl-$C_1–C_6$-alkyl, wherein the phenyl ring is unsubstituted or is substituted by one to three substituents selected from the group consisting of cyano, nitro, halogen, $C_1–C_4$-alkyl, $C_1–C_6$-haloalkyl, $C_1–C_6$-alkoxy, $C_2–C_6$-alkenyloxy, $C_3–C_6$-alkynyloxy and ($C_1–C_6$-alkoxy)carbonyl;

$R^7$ is a $C_1–C_6$-alkyl, $C_2–C_6$-alkenyl, $C_3–C_6$-alkynyl or phenyl-$C_1–C_6$-alkyl group, wherein these 4 groups are unsubstituted or are substituted by one or two substituents selected from the group consisting of halogen, $C_1–C_3$-alkoxy, $C_1–C_3$-alkoxyimino, ($C_1–C_3$-alkoxy)carbonyl, ($C_1–C_3$-alkylamino)carbonyl, di($C_1–C_3$-alkyl)aminocarbonyl and CO—N($C_1–C_3$-alkyl)-($C_1–C_3$-alkoxy), wherein the 4 last-mentioned radicals, in turn, are unsubstituted or are substituted by a ($C_1–C_3$-alkoxy)carbonyl or a $C_1–C_4$-alkoxy group;

or an agriculturally useful salt of the compound I.

2. A herbicidal composition, comprising a herbicidally effective amount of one or more hydroximic acid compound of formula I as defined in claim 1 or of an agriculturally useful salt of I and one or more inert liquid or solid carrier and optionally one or more surfactant.

3. A composition for the desiccation or defoliation of plants, comprising such an amount of one or more hydroximic acid compound of formula I as defined in claim 1 or of an agriculturally useful salt of I that it acts as a desiccant or defoliant, and one or more inert liquid or solid carrier and optionally one or more surfactant.

4. A method of controlling undesirable vegetation, which comprises allowing a herbicidally effective amount of one or more hydroximic acid compound of formula I as defined in claim 1 or of an agriculturally useful salt of I to act on plants, their environment or on seed.

5. A method for desiccation or defoliation of plants, which comprises allowing an amount effective as desiccant or defoliant of one or more hydroximic acid compound of formula I as defined in claim 1 or an agriculturally useful salt of I to act on plants.

6. The method of claim 5, wherein the treated plants are cotton plants.

7. The compound of formula I defined in claim 1, wherein X is oxygen.

8. The compound of formula I defined in claim 1, wherein Y is oxygen.

9. The compound of formula I defined in claim 1, wherein $R^1$ is $C_1$–$C_4$-alkyl or amino.

10. The compound of formula I defined in claim 1, wherein $R^1$ is methyl or amino.

11. The compound of formula I defined in claim 1, wherein $R^2$ is trifluoromethyl or trifluoroethyl.

12. The compound of formula I defined in claim 1, wherein $R^3$ is hydrogen.

13. The compound of formula I defined in claim 1, wherein $R^4$ is halogen.

14. The compound of formula I defined in claim 1, wherein $R^5$ is halogen.

15. The compound of formula I defined in claim 1, wherein $R^5$ is cyano or chlorine.

16. The compound of formula I defined in claim 1, wherein $R^6$ is $C_1$–$C_6$-alkyl.

17. The compound of formula I defined in claim 1, wherein $R^7$ is $C_1$–$C_6$-alkyl which is unsubstituted or substituted by ($C_1$–$C_3$-alkoxy)carbonyl.

18. An oxime of formula VII

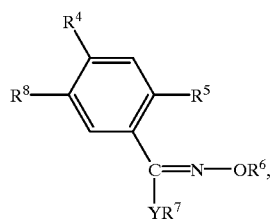

(VII)

wherein
  Y is oxygen or sulfur:
  $R^4$ is hydrogen or halogen;
  $R^5$ is cyano or halogen;
  $R^6$ is $C_1$–$C_6$-alkyl, $C_2$–$C_6$-alkenyl, $C_3$–$C_6$-alkynyl or is phenyl-$C_1$–$C_6$-alkyl, wherein the phenyl ring is unsubstituted or is substituted by one to three substituents selected from the group consisting of cyano, nitro, halogen, $C_1$–$C_4$-alkyl, $C_1$–$C_6$-haloalkyl, $C_1$–$C_6$-alkoxy, $C_2$–$C_6$-alkenyloxy, $C_3$–$C_6$-alkynyloxy and ($C_1$–$C_6$-alkoxy)carbonyl;
  $R^7$ is a $C_1$–$C_6$-alkyl, $C_2$–$C_6$-alkenyl, $C_3$–$C_6$-alkynyl or phenyl-$C_1$–$C_6$-alkyl grour, wherein these 4 groups are unsubstituted or are substituted by one or two substituents selected from the group consisting of halogen, $C_1$–$C_3$-alkoxy, $C_1$–$C_3$-alkoxyi-mino, ($C_1$–$C_3$-alkoxy)carbonyl, ($C_1$–$C_3$-alkylamino) carbonyl, di($C_1$–$C_3$-alkyl) aminocarbonyl and CO—N($C_1$–$C_3$-alkyl)-($C_1$–$C_3$-alkoxy), wherein the 4 last-mentioned radicals, in turn, are unsubstituted or are substituted by a ($C_1$–$C_3$-alkoxv)carbonyl or a $C_1$–$C_4$-alkoxy group; and
  $R^8$ is nitro, amino, isocyanato, isothiocyanato, ($C_1$–$C_6$-alkyl)carbamato or phenylcarbamato.

* * * * *

UNITED STATES PATENT AND TRADEMARK OFFICE
CERTIFICATE OF CORRECTION

PATENT NO. : 6,387,849 B1
DATED : May 14, 2002
INVENTOR(S) : Menke et al.

It is certified that error appears in the above-identified patent and that said Letters Patent is hereby corrected as shown below:

<u>Column 24,</u>
Line 26, "grour" should be -- group --;
Line 29, "alkoxyi-mino" should be -- alkoxyimino --;
Line 34, "alkoxv" should read -- alkoxy --.

Signed and Sealed this

Eighth Day of October, 2002

Attest:

Attesting Officer

JAMES E. ROGAN
*Director of the United States Patent and Trademark Office*